United States Patent [19]

Ang

[11] Patent Number: 5,646,045

[45] Date of Patent: Jul. 8, 1997

[54] CELLULOSE IN FOOD MATRIX QUANTIFICATION

[75] Inventor: Jit F. Ang, Chesterfield, Mo.

[73] Assignee: Protein Technologies International, St. Louis, Mo.

[21] Appl. No.: 443,008

[22] Filed: May 17, 1995

[51] Int. Cl.$^6$ .................................................... G01N 33/04
[52] U.S. Cl. ............................. 436/20; 426/36; 426/582; 436/164
[58] Field of Search .................. 436/20, 56, 94, 436/164; 426/36, 96, 582

[56] References Cited

PUBLICATIONS

*Journal of the Association of Official Analytical Chemist*, vol. 68, 1985, p. 399.

Casey, "Pulp and Paper Chemistry and Chemical Technology", second edition, pp. 1475–1490, (No Date Given).

Fibert Analysis Of Paper And Paperboard; TAPPI, T401–om–88 (No Publication Date Given), (No page Number Given).

*Primary Examiner*—Lyle A. Alexander
*Attorney, Agent, or Firm*—Richard B. Taylor

[57] ABSTRACT

A method of determining the quantity of particulate cellulose in a food matrix such as grated or shredded cheese by applying to the food matrix a stain having the capacity to visually selectively stain cellulose as differentiated from the food matrix, and comparing the degree of resulting coloration thereof against a standard using a series of food matrix portions having differing known quantities of stained particulate cellulose therein.

11 Claims, No Drawings

CELLULOSE IN FOOD MATRIX QUANTIFICATION

BACKGROUND OF THE INVENTION

This invention relates to food products, and particularly to a method of providing a quick, accurate determination of the amount of cellulose in a food product such as grated or shredded cheese, during production of the food product.

Cellulosic ingredients are commonly used in the food industry for a number of functionalities. In the dairy industry, cellulose (both powdered and microcrystalline) is widely used as an anti-caking agent to prevent the re-agglomeration of shredded and grated cheeses. Typical levels of usage are between only about 0.5 to 2.0 weight percent based on the weight of the cheese. The cellulose is thus widely dispersed in the food matrix so as to normally he visually undetected by the consumer, to not detract from the appearance of the food.

Although this application of cellulose is not new, it was not until recently that the quantification of cellulose in cheese has gained importance. In the past, the amount of cellulose present in these products was estimated based on the amount of cellulose usage per unit time (indirect method). A more direct method is also available using prior art. However, this Total Dietary Fiber method (published by the Association of Official and Analytical Chemists and the American Association of Cereal Chemists) is tedious and slow (takes a minimum of two days before results can be obtained). In addition, most plant quality control/assurance laboratories do not have the expertise or the capability to run this test.

The importance of a rapid method to quantify the amount of cellulose anti-caking agent in cheeses is driven by the dairy manufacturers' desire for consistency and quality in their products. By being able to rapidly determine the amount of cellulose in the cheese going through their processing line, timely adjustments can be made to the cellulose applicators to obtain the desired level of addition.

SUMMARY OF THE INVENTION

The concept of this invention is based on the principle that if a set of food samples, specifically cheese samples, containing known amounts of cellulose can be processed such that the end results would visually differentiate them, then a sample containing an unknown amount of cellulose can be matched up to the known standards. The object was to develop such a process which would also provide rapid results, indicating amounts even as small as the typical 0.5 to 2% or so by weight cellulose. Differential sample staining was conceived as being feasible since this method would be relatively simple and fast to perform. Moreover, the amount of cellulose in the sample could either be matched to a standard visually or via the use of instruments.

In the paper and pulp industry, several stains or dyes are used for the purpose of identifying the type of cellulose fibers in the pulp (e.g., tree species, type of process). Among the dyes commonly used are the Graff C-Stain, the Herzberg Stain, and the Selleger's Stain. However, as far as is known, use of these stains has been limited to only the paper and pulp industry.

This invention relates to the food industry. Specifically, this invention employs selective staining techniques for rapid quantification of cellulose ingredients in food products, particularly dairy products. A stain having the capacity to visually selectively stain cellulose, as differentiated from a food matrix, is used for determining the quantity of particulate cellulose dispersed in a food matrix. The invention is especially useful for determining the amount of cellulose anti-caking agent in shredded and grated cheeses.

In addition to providing a new, rapid quantification method for cellulose in a food matrix, this invention also offers other advantages over traditional stains used in the paper and pulp industry. One major advantage of this invention is the improved stability of the color after stain application for the necessary time to make visual and/or optical comparison. Traditional stains prepared using prior art were only color-stable for about 20 minutes after application. Stains prepared using the new teachings were stable for more than 60 minutes after initial use.

Another advantage of this invention is lower cost. Using this invention, more effective stains can be prepared at about 26% the cost of traditional stains.

These and several other objects and advantages of the invention will be apparent upon review of the following specification teachings.

DESCRIPTION OF THE PREFERRED EMBODIMENTS

The novel quantification method for indicating the quantity of cellulose dispersed in food products, even in amounts of only about 0.5 to 2% by weight has been shown by experimentation to be successful, rapid and reliable.

Three different stains were initially screened for their suitability in this novel rapid quantification method. These were the Graff "C" stain, the Herzberg stain, and the Selleger's stain. The stains were individually added to shredded Mozzarella cheese which contained 2.0% cellulose. Of the three, the Selleger's stain was least effective. It stained the cellulose gray. This color faded in less than one hour. Of the remaining two stains, the Herzberg stain was found to be better in terms of color (cellulose was stained brown). However, neither of the remaining stains provided a stable color. Therefore, most of the work following the initial screening process was focused on providing stains of improved quality and functionality for this rapid quantification in food method.

Formulation of the traditional Herzberg stain is as follows:

1. Zinc chloride solution. Dissolve 50 g of $ZnCl_2$ in 25 ml distilled water.
2. Iodine solution. Dissolve 0.25 g $I_2$ and 5.25 g KI in 12.5 ml distilled water.

Mix 25 ml of the zinc chloride solution with all of the iodine solution. Pour this mixture into a narrow cylinder and let stand until clear (or overnight). Decant the supernatant into a dark bottle and add a small amount of excess iodine for better stability during storage.

Improved new stains developed as part of this invention include the following variations:

Variation 1

1. Calcium chloride solution. Dissolve 41 g of $CaCl_2 \cdot 2H_2O$ in 25 ml distilled water.
2. Iodine solution. Dissolve 0.25 g $I_2$ and 5.25 g KI in 12.5 ml distilled water.

Mix 25 ml of the calcium chloride solution with all of the iodine solution. Pour this mixture into a container, e.g., a narrow cylinder, and let stand until clear (or overnight).

Decant the supernatant into a dark bottle and add a small amount of excess iodine for better stability during storage.

Variation 2

1. Copper chloride solution. Dissolve 62.5 g of $CuCl_2.2H_2O$ in 45 ml distilled water.
2. Iodine solution. Dissolve 0.25 g $I_2$ and 5.25 g KI in 12.5 ml distilled water.

Mix 25 ml of the copper chloride solution with all of the iodine solution. Pour this mixture into a narrow cylinder and let stand until clear (or overnight). Decant the supernatant into a dark bottle and add a small amount of excess iodine for better stability during storage.

Variation 3

1. Zinc chloride solution. Dissolve 50 g of $ZnCl_2$ in 25 ml distilled water.
2. Iodine solution. Dissolve 0.25 g $I_2$ and 4.8 g NaI in 12.5 ml distilled water.

Mix 25 ml of the zinc chloride solution with all of the iodine solution. Pour this mixture into a narrow cylinder and let stand until clear (or overnight). Decant the supernatant into a dark bottle and add a small amount of excess iodine for better stability during storage.

Variation 4

1. Calcium chloride solution. Dissolve 41 g of $CaCl_2.2H_2O$ in 25 ml distilled water.
2. Iodine solution. Dissolve 0.25 g $I_2$ and 4.8 g NaI in 12.5 ml distilled water.

Mix 25 ml of the calcium chloride solution with all of the iodine solution. Pour this mixture into a narrow cylinder and let stand until clear (or overnight). Decant the supernatant into a dark bottle and add a small amount of excess iodine for better stability during storage.

Variation 5

1. Copper chloride solution. Dissolve 62.5 g of $CuCl_2.2H_2O$ in 45 ml distilled water.
2. Iodine solution. Dissolve 0.25 g $I_2$ and 4.8 g NaI in 12.5 ml distilled water.

Mix 25 ml of the copper chloride solution with all of the iodine solution. Pour this mixture into a narrow cylinder and let stand until clear (or overnight). Decant the supernatant into a dark bottle and add a small amount of excess iodine for better stability during storage.

Variation 6

1. Sodium chloride solution. Dissolve 21.4 g of NaCl in 55 ml distilled water.
2. Iodine solution. Dissolve 0.25 g $I_2$ and 5.25 g KI in 12.5 ml distilled water.

Mix 25 ml of the sodium chloride solution with all of the iodine solution. Pour this mixture into a narrow cylinder and let stand until clear (or overnight). Decant the supernatant into a dark bottle and add a small amount of excess iodine for better stability during storage.

The following procedures were used to evaluate the stains prepared from above:

1. Place 50 g of shredded Mozzarella cheese sample (with different kinds of cellulose anti-caking agent added at 2.0% level) on an 8" white Styrofoam plate. Spread the cheese sample out evenly to cover the entire plate.
2. Using a spray bottle, spray the cheese sample with 5 ml of stain.
3. Record visual observations every 10 minutes and note any color changes.

Results of color changes obtained from this testing are summarized below:

| Herzberg | Var. 1 | Var. 2 | Var. 3 | Var. 4 | Var. 5 | Var. 6 |
| --- | --- | --- | --- | --- | --- | --- |
| Sample: Control Mozzarella cheese (no cellulose added) | | | | | | |
| Yellow | Yellow | Green/Blue | Yellow | Yellow | Green/Blue | Yellow |
| Sample: Mozzarella cheese containing 2.0% of a 35-micron powdered cellulose | | | | | | |
| Brown | Dark Brown | Dark Green/Blue | Dark Brown | Dark Brown | Dark Green/Blue | Blue/Gray |
| Sample: Mozzarella cheese containing 2.0% of a 120-micron powdered cellulose | | | | | | |
| Brown | Dark Brown | Dark Green/Blue | Dark Brown | Dark Brown | Dark Green/Blue | Blue/Gray |

| Sample | Color Fade Time (minutes) | Other Observations |
| --- | --- | --- |
| Herberg | <20 | |
| Var. 1 | >60 | Cellulose fibers were easily identified. |
| Var. 2 | <30 | Within 30 minutes, sample turned dirty gray, making cellulose identification difficult |
| Var. 3 | 30 | |
| Var. 4 | >60 | Similar to Var. 1 |
| Var. 5 | 30 | After 30 minutes, sample turned dirty gray, making cellulose identification difficult |
| Var. 6 | <20 | After 20 minutes, sample turned dirty moldy gray, making cellulose identification difficult |

Based on these test results, the stain prepared using Variation No. 4 was judged to be best for this purpose. This was closely followed by Variation No. 1. In all variations, stains were either equally or more stable than the traditional Herzberg stain.

In developing the rapid quantification test for cellulose in cheeses, a set of standards (cheese samples which have known amounts of cellulose added) are prepared and stained prior to the analysis of the unknown sample. Preparation of these standards is one major reason why the color stability of a stain is important for this application. Standards can be prepared to contain from 0.0 to 3.0% cellulose at either 0.5, 0.25% or any other appropriate intervals. Final quantification can be achieved via two methods: visual comparison of unknown against standards, or color measurement (instrumental method) of unknown using an appropriate colorimeter or an equivalent instrument and comparing this reading against those obtained from standards. The standards could be previously stained food products or photographic reproductions thereof.

To further validate the invention, the stain from Variation No. 4 was used to provide rapid quantification of other cellulosic anti-caking agents as well as common ingredients which do not offer anti-caking function in shredded cheese. Procedures for this determination were the same as those previously outlined. Results obtained are depicted below:

| Cheese Additive | Observations |
| --- | --- |
| None-Control | Yellow-golden color. Mozzarella cheese did not change color. |
| Microcrystalline Cellulose | Cellulose fibers were colored brown and the color faded after one hour. |
| Sucrose | Yellow-golden color. Mozzarella cheese and the sucrose did not change color. |
| Lactose | Yellow-golden color. Mozzarella cheese and the sucrose did not change color. |
| Rice Powder | Entire sample turned gray immediately. |
| Soy Fiber | Brown specks were observed, indicative of the presence of soy fiber. This color faded after one hour. |
| Corn Starch | Entire sample turned blue-black immediately, confirming the reaction between starch and iodine present in the stain. |

The above examples and details comprise the preferred manner of performing the invention. However, those in the food processing field of endeavor can provide variations within the concept presented for specific applications. Therefore, it is intended that the invention not be limited by the detailed specification, but only by the scope of the appended claims and the equivalents thereof.

The embodiments of the invention in which an exclusive property or privilege is claimed are defined as follows:

1. A method of determining the quantity of particulate cellulose dispersed in a food matrix comprising the steps of applying to the food matrix a stain having the capacity to visually selectively color cellulose as differentiated from the food matrix, and comparing the degree of resulting coloration of the food matrix against a standard.

2. The method in claim 1 wherein said step of comparing is clone visually.

3. The method in claim 1 wherein said step of comparing is done by instrumentation.

4. The method in claim 1 wherein said standard comprises a stained physical food matrix containing a known amount of cellulose.

5. The method in claim 1 wherein said standard comprises a visual reproduction of a stained food matrix containing a known amount of cellulose.

6. The method in claim 1 wherein said stain comprises a calcium chloride and iodine solution.

7. The method in claim 1 wherein said stain comprises a copper chloride and iodine solution.

8. The method in claim 1 wherein said stain comprises a zinc chloride and iodine solution.

9. The method in claim 1 wherein said standard comprises a series of food matrix portions respectively containing different known quantities of stained particulate cellulose therein.

10. The method in claim 9 wherein said step of applying said stain to the food matrix uses the same type of stain as said stained particulate cellulose in said food matrix portions.

11. The method in claim 1 wherein said food matrix comprises grated or shredded cheese.

* * * * *